United States Patent
Tafas et al.

(10) Patent No.: US 7,639,139 B2
(45) Date of Patent: Dec. 29, 2009

(54) SYSTEM FOR AUTOMATICALLY LOCATING AND MANIPULATING POSITIONS ON AN OBJECT

(75) Inventors: Triantafyllos P. Tafas, Rocky Hill, CT (US); Youngmin Kim, Wallingford, CT (US)

(73) Assignee: Ikonisys, Inc., New Haven, CT (US)

( * ) Notice: Subject to any disclaimer, the term of this patent is extended or adjusted under 35 U.S.C. 154(b) by 336 days.

(21) Appl. No.: 11/693,551

(22) Filed: Mar. 29, 2007

(65) Prior Publication Data
US 2008/0238674 A1    Oct. 2, 2008

Related U.S. Application Data

(63) Continuation of application No. 10/870,111, filed on Jun. 17, 2004, now Pat. No. 7,199,712.

(51) Int. Cl.
*G08B 13/14* (2006.01)
*G02B 21/00* (2006.01)

(52) U.S. Cl. .................................. 340/572.1; 359/368

(58) Field of Classification Search ............. 340/539.1, 340/539.11–539.19, 571, 505, 10.1–10.52, 340/572.1–572.9, 568.1–568.8; 700/362, 700/302, 56–66; 427/2.11–2.13; 359/368–398; 356/2, 3, 3.01, 3.09, 3.1, 3.11, 3.16, 614–624, 356/391–393; 342/126–147; 378/43, 177, 378/181, 205; 399/8, 26; 250/201.1–201.8, 250/559.29, 559.3, 559.31–559.38, 206.2; 382/286–292, 321–325, 128–134
See application file for complete search history.

(56) References Cited

U.S. PATENT DOCUMENTS

| | | | |
|---|---|---|---|
| 4,183,614 A | 1/1980 | Feldman | |
| 4,190,314 A | 2/1980 | Goldsmith | |
| 4,513,438 A | 4/1985 | Graham et al. | |
| 4,651,203 A | 3/1987 | Peterson | |
| 5,602,674 A | 2/1997 | Weissman et al. | |
| 5,694,212 A | 12/1997 | Weissman | |
| 5,812,312 A | 9/1998 | Lorincz | |
| 5,963,368 A | 10/1999 | Domanik et al. | |
| 6,006,140 A | 12/1999 | Carter | |
| 6,104,291 A | 8/2000 | Beauvillier et al. | |
| 6,236,223 B1 | 5/2001 | Brady et al. | |
| 6,567,214 B2 | 5/2003 | Lorincz | |

(Continued)

FOREIGN PATENT DOCUMENTS

JP    2005/128868    5/2005

(Continued)

*Primary Examiner*—Jennifer Mehmood
(74) *Attorney, Agent, or Firm*—Kelley Drye & Warren LLP

(57) ABSTRACT

A system for automatically locating positions on an object and uniquely identifying the object employing an electronic tag positioned in or on the object. The system utilizes a plurality of sensors to locate the electronic tag and identify the object, and triangulation techniques to locate positions on the object where the object may be manipulated according to instructions coded with respect to the positions. Advantageously, the present invention may be used for automatically locating specimens on a microscope slide without regards to their positions on the slide, and for uniquely labeling a microscope slide.

12 Claims, 4 Drawing Sheets

U.S. PATENT DOCUMENTS

| | | |
|---|---|---|
| 6,714,121 B1 | 3/2004 | Moore |
| 6,750,769 B1 | 6/2004 | Smith |
| 7,023,356 B2 | 4/2006 | Burkhardt et al. |
| 7,030,736 B2 | 4/2006 | Bouchard et al. |
| 7,167,305 B2 * | 1/2007 | Ogihara .................. 359/383 |
| 7,215,467 B2 * | 5/2007 | Nakagawa ............... 359/380 |
| 2002/0030598 A1 | 3/2002 | Dombrowski et al. |
| 2002/0061127 A1 * | 5/2002 | Bacus et al. ............. 382/128 |
| 2004/0114218 A1 * | 6/2004 | Karlsson et al. ......... 359/368 |
| 2005/0051614 A1 | 3/2005 | Albany |
| 2005/0123181 A1 | 6/2005 | Freund et al. |
| 2005/0242957 A1 | 11/2005 | Lindsay et al. |

FOREIGN PATENT DOCUMENTS

| | | |
|---|---|---|
| WO | WO 2005/121865 A1 | 12/2005 |

* cited by examiner

SYSTEM FOR AUTOMATICALLY LOCATING AND MANIPULATING POSITIONS ON AN OBJECT

CROSS-REFERENCE TO RELATED APPLICATIONS

This is a continuation application of U.S. patent application Ser. No. 10/870,111, filed Jun. 17, 2004, now U.S. Pat. No. 7,199,712, the entire contents of which is incorporated herein by reference in its entirety.

FIELD OF INVENTION

This invention is related to a system and assembly for automatically locating positions along an object and for providing object identification. Advantageously, the present invention may be used for automatically locating specimens on a microscope slide without regards to their positions on the slide, and for uniquely labeling a microscope slide.

BACKGROUND OF INVENTION

The identification of a desired position on an object in automated processes is often a laborious task. Items in automated processes are typically placed in restrained area to allow for directed manipulation at desired positions of the objects based upon known dimensions of the object and knowledge of the position of predetermined reference points associated with the object. For example, numerous conventional microscope slides incorporate internal grids to locate a position on the microscope slides with respect to the viewing lens of a microscope. An external grid placed on the stage of the microscope may also be used to map the location of an object on the slide.

In U.S. Pat. No. 4,183,614, Feldman discloses a microscope slide and method of making the same, providing on a substantially transparent substrate, an extremely closely spaced grid pattern of a film less transparent than the substrate, with the pattern produced by photochemical etching, and with the film typically an iridized metal oxide film. Goldsmith in U.S. Pat. No. 4,190,314 also disclose a microscope slide having a plurality of spaced parallel lines permanently placed on the slide with the space between each successive pair of lines defining a reference plane. The spacing between each pair of lines corresponds to the field of view produced by the particular microscope lens and eyepiece being utilized so that when a viewer makes a viewing pass across each successive reference plane that the specimen smear is located in, by keeping the lines continuously in the field of view during each pass, the entire area of the smear is viewed.

In another U.S. Pat. No. 5,694,212, Weissman shows a method and device for the calibration of microscope slides for use in accurate and repeatable position location and relocation of specific areas of a specimen on the slide, particularly with use of computer correlated location of specimen events. Weissman discloses a calibration device, which is placed on a microscope stage, against a fixed position portion of the slide holder. The viewfinder of the lens is then moved to superimpose and enter a calibration mark directly on two opposite corners of the calibration slide, or on location marks on the calibration slide which are a pre-set distance from such opposite corners. Entry of the corner positions locates a diagonal line of the appropriate length and of a particular slope, relative to the x-y axes of microscope stage movement. Deviation of the obtained slope from a predetermined slope for a true orthogonal position for the slide is calculated and used to compensate for deviations in locating and relocating areas on a specimen subsequently positioned on the specimen holder. Weissman, et al., disclose a computerized specimen encoder in U.S. Pat. No. 5,602,674. The slide encoder is attached to a movable microscope stage, whereby X-Y plane movement and location, is correlated to examination of a specimen on an identified slide, with information marking and location being directly correspondingly written on computer storage media, during the examination. The information marking is in the form of computer generated indicia which are placed at a computer image location of the slide at predetermined time intervals. Subsequent use of the computer-stored information, coupled with the slide encoder, in a slide re-examination, permits independent retrieval of such information and location on the slide.

A self-staining microscopic slide designed for immediate staining and viewing of cells in biological fluid and tissue samples is described in U.S. Pat. No. 5,812,312 by Lorinrz. The pre-prepared microscope slide preferably has a supravital fluorescent stain applied thereon, which is overlaid with a transparent tape or film. During use, the film is peeled back to expose the stain so that a sample can be applied thereon for intermixture therewith. The film is then replaced over the stained sample to act as a cover slip for immediate viewing. Living cells and microorganisms are rendered visible and cellular dysmorphology readily ascertained. The slide can include reference standards to facilitate microscope focusing, and to allow measurements of cells and microorganisms. Lorinez also discloses a microscope slide having a well formed therein, wherein the well is filled with culture media, and method for use in U.S. Pat. No. 6,567,214. The slide is designed for on-site collection, staining, and viewing of cells in biological fluid and tissue samples, preferably with an epi-fluorescence microscope. The slide permits quick point-of-care screening of any biological fluid or tissue sample for presence of infectious agents, after which, the slide can be transported to a central lab for culture and/or definitive identification.

A specimen management system in a clinical laboratory is disclosed in U.S. Pat. No. 5,963,368 by Domanik, et al. The system comprises specimens and a computer controlled instrument. Each specimen includes a biological sample and an identifier which is unique to the specimen to which it is applied. The computer controlled instrument includes a reader for automatically logging and verifying the specimen to be analyzed, and a print head for modifying the identifier to indicate whether the specimen has been analyzed and whether the sample includes any abnormalities. The print head is also used to indicate whether the specimen has been reanalyzed. Further, the print head works to print symbols adjacent the locations of the abnormalities in the sample.

A method and apparatus for tracking materials automatically is described by Moore in U.S. Pat. No. 6,714,121. A passive RFID tag is used with a material tracking system capable of real-time location and identification of items in production and storage areas. RFID tags are attached to the item to be tracked, remote sending antennas are placed at each remote location to be monitored, interrogators with several antenna inputs are connected to the sending antennas to multiplex the antenna signals, and a host computer communicates with the interrogators to determine item locations precisely.

The contents of the entire prior art references cited herein are incorporated by reference.

From the foregoing it can be understood by those having ordinary skill in the art that although the systems and methods described above are adequate for locating objects themselves, they lack the capability of automatically locating positions along an object, with or without grids or tags on the object. It will also be understood by those skilled in the art that there is a need for not only locating an object, such as a microscope slide under a microscope, but also for marking specimens at different locations on the slide along with their identities and their conditions.

SUMMARY OF INVENTION

An embodiment of the present invention provides a system for automatically locating positions on an object and uniquely identifying the objects employing an electronic tag positioned in or on the object. In a preferred embodiment, the tag has an identifier code. A plurality of remote devices is capable of locating and activating the tag. A microprocessor communicates with the plurality of remote devices and a manipulator of the object. The microprocessor records a position of the tag, and commands the manipulator to perform manipulations at selected positions on the object relative to the position of the tag. A display associated with the microprocessor presents the identifier code, location and information related to the positions on the object.

Another embodiment of the present invention comprises a system for automatically locating and identifying a specimen on a microscope slide. The system comprises a substrate having a first region for receiving a sample of specimens and a second region for receiving a tag representing an identifier code for the specimens. A plurality of remotely configured devices capable of emitting signals can activate the tag from a distance. A viewer, having a viewing lens, is positioned over the substrate. The viewer has a microprocessor capable of communicating with the plurality of devices. The microprocessor records and stores the position of the viewer relative to the signals received from the remote devices corresponding to the location of the specimens on the substrate. The microprocessor records and stores the identifier code for the sample of specimens. A display associated with the viewer is configured to present the identifier code and location of each of the specimens in the sample.

In another aspect of the embodiment of the present invention, a method provides for automatically locating and identifying specimens deposited on a microscope slide incorporating an RFID system. The system comprises a tag on the slide and a plurality of sensors capable of communicating with the tag. The system further comprises a microscope to view the specimens, a microscope stage to receive the slide, and a microprocessor to perform positional calculations based on signals communicated between the tag and the sensors. The method involves depositing biological specimens on the slide, the specimens having identifier codes recorded in the tag; loading the slide on the microscope stage; activating the tag utilizing signals emanating from the sensors; collecting signals traversing between the tag and the plurality of sensors and transmitting the signals to the microprocessor, the microprocessor computing the position of the slide on the stage; and automatically commanding the stage to move to a position under the microscope suitable for viewing a specimen having a matching preassigned code stored in the memory bank associated with the microprocessor.

Another aspect of the present invention provides an apparatus for automatically positioning a microscope slide on a microscope stage. A microcomputer, having a stored digital map of the surface of the microscope slide, communicates with the stage. A plurality of position broadcasting devices is mounted on the microscope slide. The devices broadcast in the form of electromagnetic radiation. A receiver capable of viewing the radiation transmits a corresponding signal to the microcomputer. The microcomputer analyzes the signal and calculates the position of the slide on the stage. The microcomputer then commands the stage to move to a predefined position on the surface of the slide which corresponds to the location of a specimen to be viewed under the microscope.

DETAILED DESCRIPTION

FIG. 1 shows an embodiment of a system 10 involving an assembly of components for locating an object 20 as well as any position or point 30 along or on the object It will be understood that the object could be any animate or inanimate object having a body. Incorporated therein or thereon the object is a tag, preferably an electronic tag comprising a radio frequency identifier device (RFID). It is an aspect of the present invention that the tag is configured to operate cooperatively with an assembly of devices, such as 40, 50 and 60, positioned remotely as shown in FIG. 1. Each device is capable of sensing or reading the RFID and determining the position of the reading source (e.g., electromagnetic beam), on the object by use of the tag as a positional reference point. Then, using a method of triangulation, any point on the object can be determined precisely with the tag as a reference point, as described below.

Figure 1A:
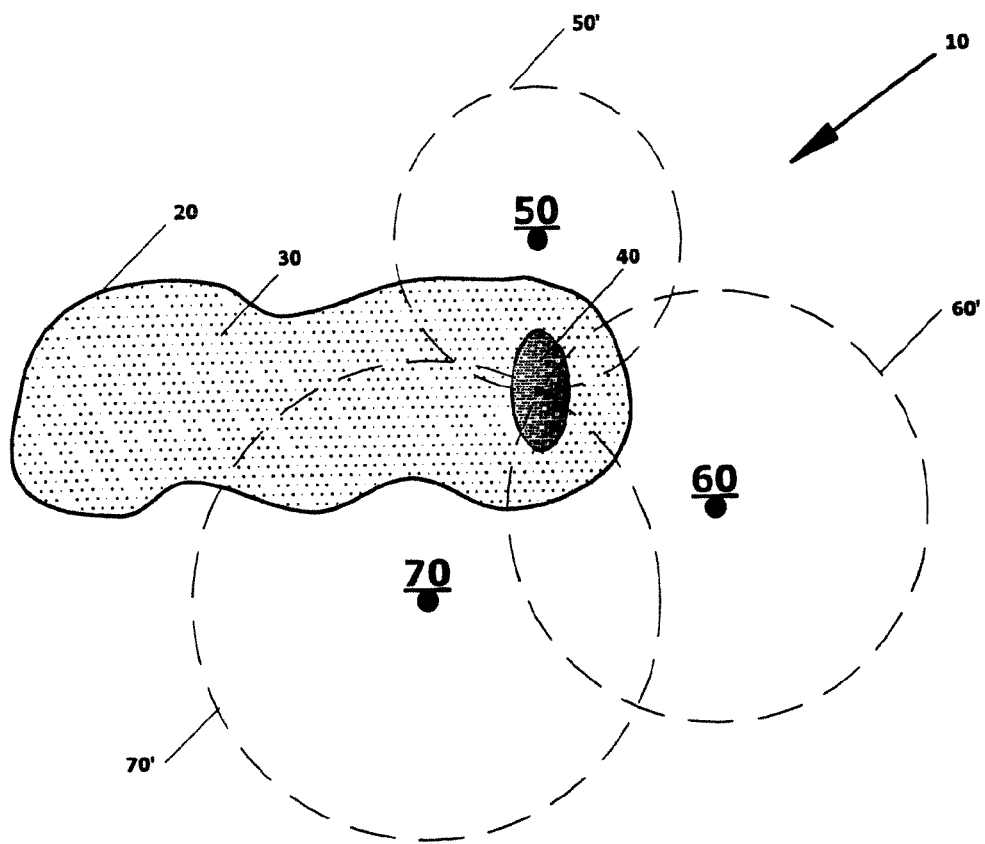
FIGS. 1a and 1b are schematic drawings showing an embodiment of components of a system for providing object identification and for automatically locating positions along an object using a triangulation method, according to the present invention.
Figure 1B:
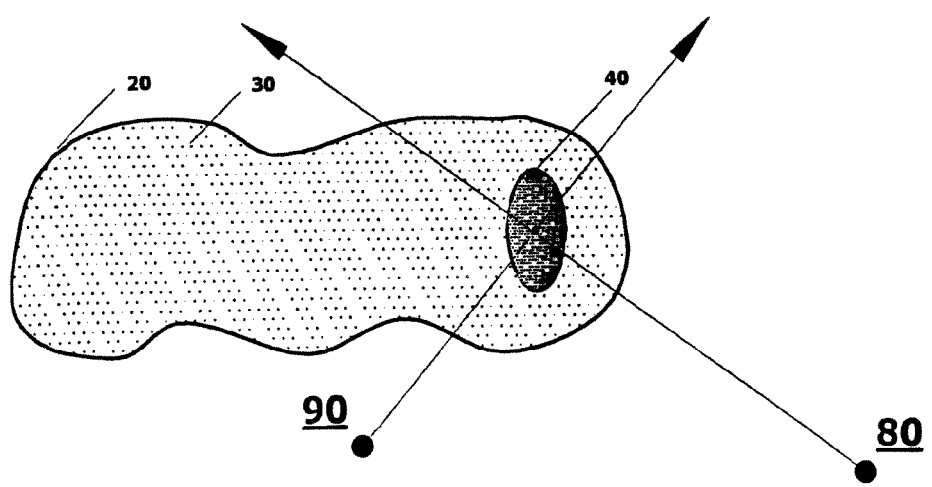

Method of triangulation involves a process by which the location of a radio transmitter is determined by measuring either the radial distance, or the direction, of the received signal at two or three different points. The position of tag 40, and hence that of object 20 is determined by measuring the relative time delays in the radio waves 50', 60', 70' between the RFID tag 40 and the three respective sensors 50, 60 and 70, as shown in FIG. 1a. As an alternate method, directional antennas may be used at two sensors 80, 90 to determine the position of the RFID tag 20, as shown in FIG. 1b. Directional antennas emit a directional signal with two parts, known as the reference phase signal and the variable phase signal. The directional signal is transmitted in such a way that the electrical phase angle between the two components differs by the exact number of degrees that the receiving tag is away from a predetermined radial from the antenna. It will be appreciated by those skilled in the art that, in this manner, the positions of points 30 on object 20 relative to the position of tag 40 can be determined with high accuracy and the conventional systems for monitoring movements using linear or rotary encoders may be replaced with the RFID system of the present invention.

Figure 2:
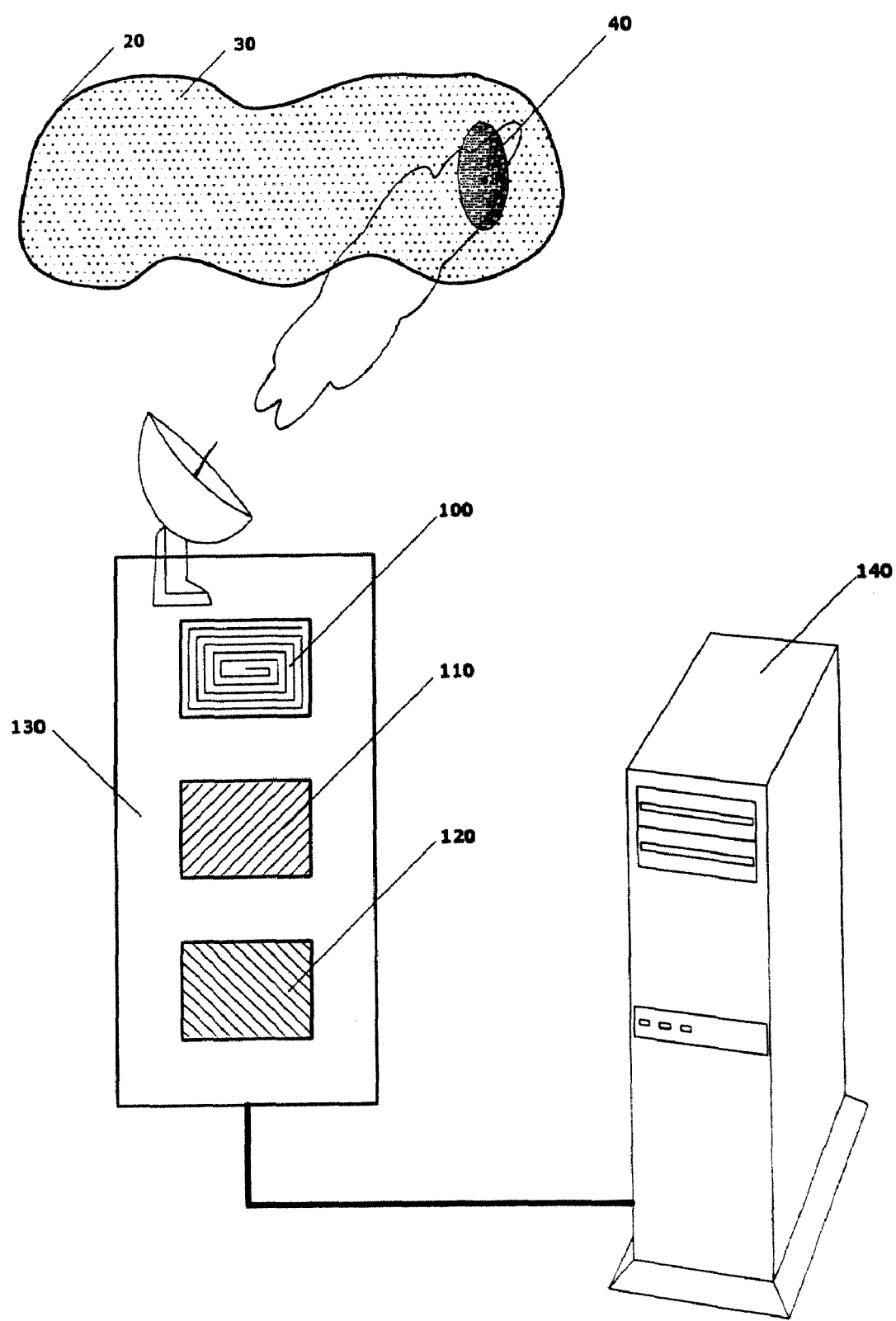
FIG. 2 is a schematic drawing showing an assembly of the components of a system for automatically locating positions along an object and for providing object identification, according to the present invention.

The RFID system of the present invention operates cooperatively incorporating an antenna or flat coil, a transceiver with a decoder and a radio frequency (RF) tag electronically programmed with unique information. In an aspect of the present RFID system shown schematically in FIG. 2, antenna 100 is packaged together with transceiver 110 and decoder 120 to become a reader sensor, also known as interrogator 130. Antenna 100 performs the function of a conduit between RF tag 40 and transceiver 110, which controls the system's data acquisition and communication. Antenna 100 emits electromagnetic radio signals to activate tag 40 and read the positional data of the tag. The tag may also include information regarding the identification of a particular object 20, such as a serial number, or other information pertaining to the object. The reader decodes the data encoded in the tag's integrated circuit (silicon chip) and the data is passed onto a microprocessor in host computer 140 shown in FIG. 2. The presence of the electromagnetic field emitted by the antenna can be continuous during the operation of the microscopy. Where constant interrogation is not required, the field can be activated by a sensor under the control of the computer 140. Furthermore, information can be both written and read onto the tag remotely by sensor(s) 130.

It is preferred that the RFID tag 40 of the present invention comprise a passive tag without a separate external power source and obtain operating power generated from the reader sensor 130. It is also preferred that the frequency range is in between about 30 KHz and 500 KHz, though high-frequency ranges of between about 850 MHz to 950 MHz and 2.4 GHz to 2.5 GHz may also be used in applications for higher read ranges.

It will be apparent to those skilled in the art that the system described above, without limitation, can be adapted to other applications where automatic location and identification of objects and positions along the objects are required. The present invention discloses the use of Radio Frequency Identifier Devices (RFID) formed onto tags, which in turn are "tagged" onto objects for the purposes of locating and identifying the objects. The tags may include information as an aid in characterizing the objects further, For example, a tag on a piece of lumber, among many others in a lumberyard say, would help locate that lumber as well as providing processing instructions as to what shape and dimensions it should be cut. The use of RFID tags as disclosed below, especially in laboratory microscopy, provides significant advantages over conventional methods of locating and identifying objects.

Figure 3:
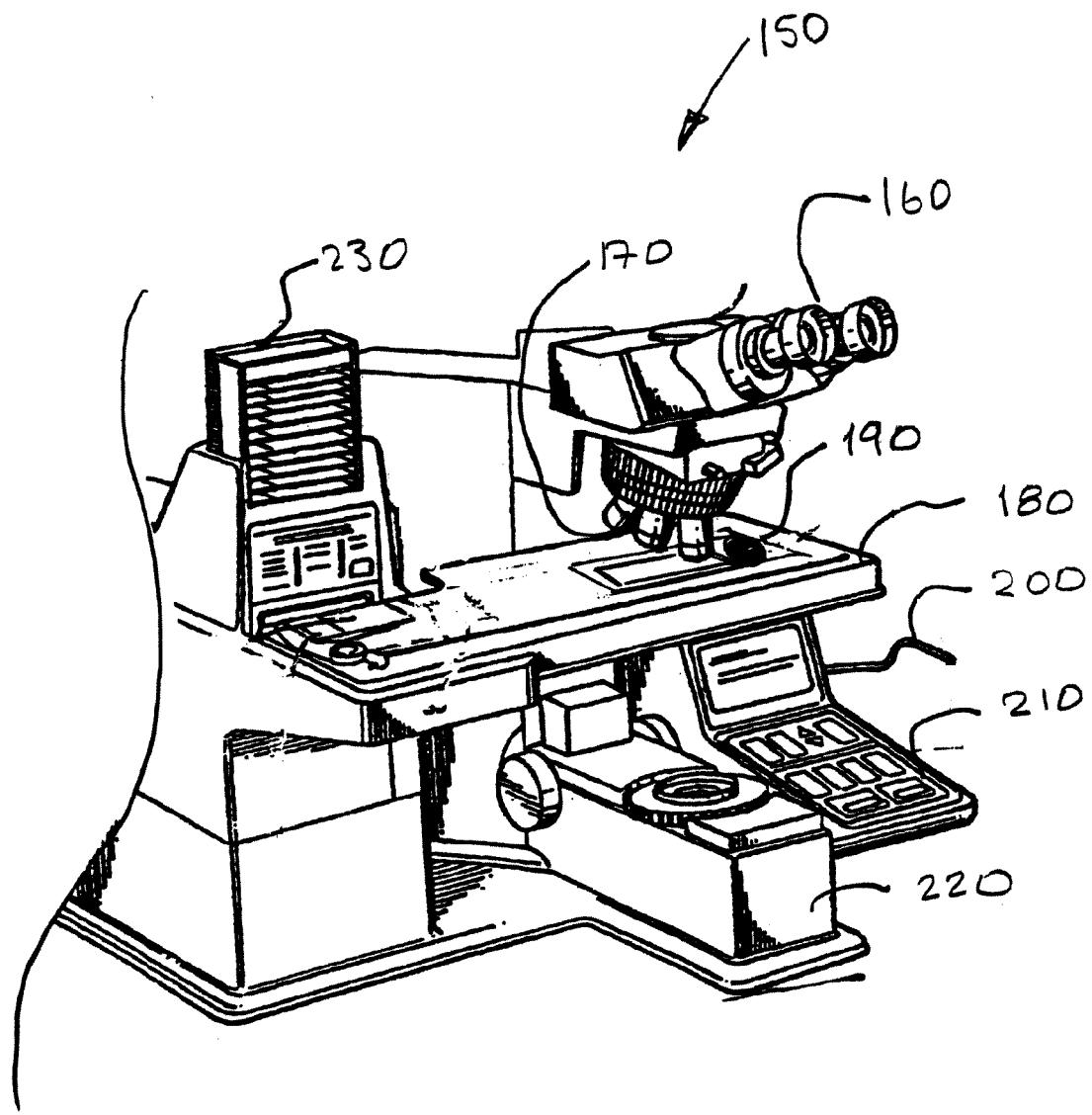
FIG. 3 is an aspect of an embodiment of the present invention showing a microscopy system incorporating the use of a Radio Frequency Identifier Device (RFID) system, according to the present invention.

Referring to FIG. 3, in accordance with one aspect of the present invention, there is provided a system and a method for recording information pertaining to source of biological material stored on a microscope slide and for monitoring the movement of microscope slides with respect to the viewing lens of a microscope in such a manner so as to permit one to repeatedly and efficiently locate biological materials of interest on the microscope slide. The method and system employ a microscope slide having incorporated thereon a radio frequency identifier device (RFID) and a RFID reader capable of reading the RFID and determining position of the reading source, e.g., electromagnetic beam, on the microscope slide by use of the RFID as a positional reference point. The system and method have several uses, including automated/fast Fluorescence in situ Hybridization, to determine from which such biological material was harvested, to repeatedly determine the position of material on the microscope slide preferably in an automated manner. The disclosed system and method greatly reduces the time that is typically spent in reviewing biological material specimens under the microscope.

In an embodiment of the present invention, FIG. 3 shows a portion of a microscope 150 used in a clinical laboratory for analysis of biological specimens deposited on a microscopy slide. Microscope 150 typically includes an eye-piece 160, objective lens 170, a microscope stage 180 on which a microscope slide 190 is mounted. The stage can be positioned under the microscope either manually by moving a lever 200 or by using a control panel 210 programmed to perform such functions. Microscope 150 and its associated accessories, including a multiple slide loading system, such as a cassette 230 for example, may be an integral part of console 220, as shown in FIG. 3. As these microscopy features are well known in the art and that they are not significant to the invention, they are not described in detail here in order not to unnecessarily obscure the present invention.

Figure 4:
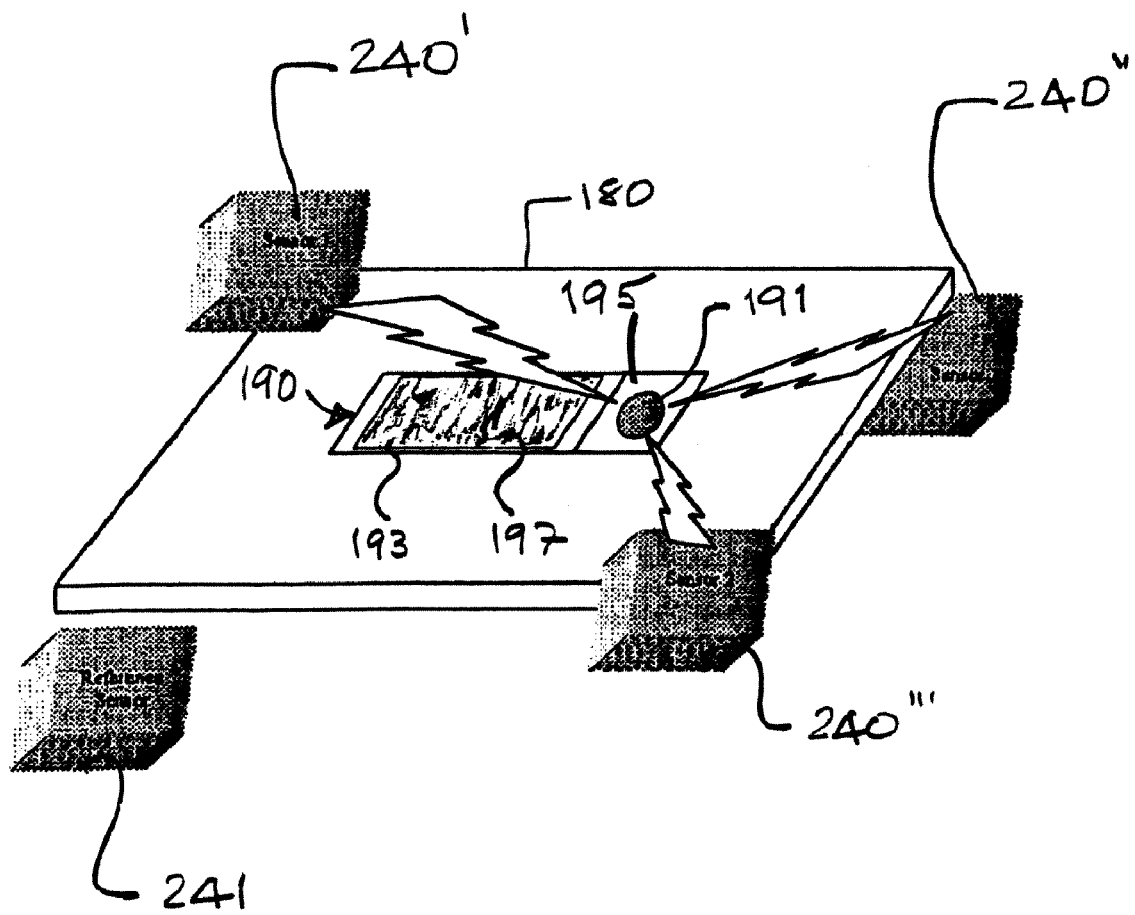
FIG. 4 is another aspect of an embodiment of the present invention showing the integration of an RFID device onto a microscope slide, according to the present invention.

An embodiment of the present invention shown in FIG. 4 incorporates a plurality of sensors 240', 240", 240''' that operate cooperatively with an electronic tag 191 integrated onto the microscope slide 190 of the present invention. Tag 190 comprises a radio frequency identifier (RFID) device. Slide 190 includes an elongate first region 193 and a second region 195. A biological specimen 197 is centrally positioned in region 193 and RF tag 191 is located in region 195. The microscope slide and a cover slip (not shown), which overlies the specimen, comprise glass although plastic can also be used. Sensors 240 may be configured in areas including on and around console 220 of FIG. 3, but within proximity of RFID tag 191. Sensors 240 have the capability of sensing the relative location of tag 191 independent of each other so that the location of the tag, and hence that of slide 190 on microscope stage 180 can be determined relative to the objective lens 170 of microscope 150 of FIG. 3, using a method of triangulation as described above. An additional reference sensor 241 can be used for added accuracy and serve as a backup.

In operation, a plurality of microscope slides 190 are tagged with RFIDs 191 bearing information corresponding to a unique ID (identification) of the specimens that will be mounted on the slides. The radio frequency emitting component of the RFIDs as well as the unique ID information may be formed on a silicon chip using any one of the well-known integrated circuit (IC) chip technologies, and the chip mounted onto the slide by using surface mount technologies also known in the art. It is preferred that the ID information for each of the slides is entered into a data base in a computer associated with the microscope system 150 shown in FIG. 3. In a separate operation (not shown), a plurality of biological specimens are mounted onto slides having the correspondingly tagged information. The slides are then loaded into a cassette 230 or other carrier (e.g., a rack or carrousel). The slides are then fed onto the microscope stage 180, either sequentially or in another sequence as commanded by a computer. As a slide is positioned on the microscope stage, it becomes into view of a plurality of sensors, and its position is automatically calculated using either one of the methods shown in FIGS. 1a and 1b. The position of the slide on the stage is transmitted to the computer. The slide can then be moved in any direction, including lateral and vertical directions (x, y and z) under the microscope for examination of the biological sample. The movement of the stage can follow a preprogrammed sequence automatically, or follow the command from an operator operating a key board, or a control panel 210 such as shown in FIG. 3. The position of the stage and hence that of the microscope slide can be monitored continuously or incrementally by the sensor readers in reference to the RFID, and any observed phenomenon (for example, abnormalities) under the microscope can be entered into the computer at the corresponding locations of biological specimens. Furthermore, images of expected abnormalities can be stored in a data base in the computer, and any such matching abnormalities that are encountered in biological cells, for example, can be automatically recorded at their respective locations. During a subsequent examination of the same sample, a particular cell of a particular abnormality can then be brought into view under the microscope instantly and automatically using the RFID triangulation system and methodology of the present invention.

In addition to monitoring the movement of a microcopy slide on a microscope stage, the RFID system can also be used as a quality assurance system in process oriented environments. In biomedical laboratories, for example, certain reagents need to be kept in controlled environmental conditions, e.g., in refrigerators. Vials containing such reagents have to be removed from the refrigerator for small periods of time. This removal from controlled environment often affects the quality of the reagent as temperature changes alter its chemical or biological consistency. Vials bearing RFID tags can be automatically monitored using a network of sensors in a laboratory environment. The system can keep track of the temperature change cycles and signal to the user so that appropriate measures are taken with the particular vial.

The RFID system can also be used in a number of situations where accurately locating an RFID-tagged item is important. An example is a security system for identifying the position of a particular item in a closed system, such as passengers and their own luggage in an airplane. In this system, an RFID tag on the passenger ticket and labels attached to the luggage can connect passengers with their pieces of luggage. At any point in time, a network of sensors positioned in the cabin of an airliner, for example, can record all pieces of luggage entering the cabin and relate them to the individual passenger through his/her ticket tag. Luggage identity can be checked against records from the passenger check-in, while unregistered pieces of luggage will be identifiable when a passenger enters the airplane. Additionally, the tags can be updated when a particular piece of luggage passes through a security check. In this manner, the exact location of all pieces of luggage in the airplane will be known. Thus, the system can immediately signal for items left behind when passengers deplane without them.

While the invention has been particularly shown and described with reference to the embodiments thereof, it will be understood by those skilled in the art that various changes in form and details may be made without departing from the spirit and scope of the invention.

What is claimed is:

1. A system comprising:
    a substrate having a first region for receiving a sample of specimens and a second region containing a tag;
    a plurality of remote devices located at known positions that emit first signals that remotely activate said tag on said substrate, said tag transmits, when activated, second signals;
    a viewer device positioned over said substrate, said viewer device having a microprocessor communicating with said plurality of remote devices;
    said microprocessor operatively configured to determine, record and store a position of said tag based on said second signals wherein said position of said tag is a positional reference point.

2. The system according to claim 1, wherein said substrate is a microscope slide.

3. The system according to claim 1, wherein said viewer device is a microscope.

4. The system according to claim 1, wherein said sample of specimens further comprise biological cells.

5. The system according to claim 1, wherein said tag comprises a radio frequency identifier device (RFID).

6. The system according to claim 5, wherein said tag comprises a passive RFID.

7. The system according to claim 1, wherein said tag comprises a transponder device formed as an integrated circuit chip.

8. The system according to claim 1, wherein said tag contains data.

9. The system according to claim 1, wherein said plurality of remote devices comprise electronic sensors that emit electromagnetic radiation.

10. The system according to claim 1, wherein said plurality of remote devices comprise electronic interrogators.

11. The system according to claim 1, wherein said microprocessor communicates with said plurality of remote devices electromagnetically.

12. The system according to claim 1, wherein said microprocessor uses triangulation techniques to compute a position of said tag relative to a position of a microscope said substrate.

* * * * *